United States Patent [19]

Andresen et al.

[11] Patent Number: 4,740,298
[45] Date of Patent: * Apr. 26, 1988

[54] CHROMATOGRAPHY COLUMN/MOVING BELT INTERFACE

[75] Inventors: Brian D. Andresen, Pleasanton; Vinit Saxena, Pinole, both of Calif.

[73] Assignee: Sepragen Corporation, San Leandro, Calif.

[*] Notice: The portion of the term of this patent subsequent to Dec. 9, 2003 has been disclaimed.

[21] Appl. No.: 904,912

[22] Filed: Sep. 8, 1986

[51] Int. Cl.$^4$ ............................................. B01D 15/08
[52] U.S. Cl. ............................... 210/198.3; 73/61.1 C; 210/198.2; 250/288; 422/66; 422/70; 436/44; 436/161
[58] Field of Search ..................... 210/656, 658, 198.2, 210/198.3; 422/70, 66; 73/61.1 C; 250/288 A; 436/161, 44

[56] References Cited

U.S. PATENT DOCUMENTS

| | | | |
|---|---|---|---|
| 2,708,519 | 5/1955 | Novak | 422/70 |
| 3,754,654 | 8/1973 | Nybom | 210/198.3 |
| 4,055,987 | 11/1977 | McFadden | 250/288 A |
| 4,178,507 | 12/1979 | Brunnee | 250/288 A |
| 4,476,017 | 10/1984 | Scharff | 210/198.2 |
| 4,570,068 | 2/1986 | Sakairi | 250/288 A |
| 4,594,506 | 6/1986 | Ghaderi | 250/288 A |
| 4,627,918 | 12/1986 | Saxena | 210/198.2 |

FOREIGN PATENT DOCUMENTS 152747  8/1985  European Pat. Off. ........ 250/288 A

OTHER PUBLICATIONS

Smith, "Liquid Chromatography-Mass Spectrometry with Electron Impact and Fast Ion Bombardment with a Ribbon Storage," Analytical Chemistry, vol. 53, No. 11, pp. 1603-1611.
Tsuge, "Vacuum Nebulizing Interface for Direct Coupling of Micro-Liquid Chromatograph and Mass Spectrometer," Analytical Chemistry, vol. 51, Jan. 1979, pp. 166-169.
Takenuchi, "On-Line Coupling of a Micro-Liquid Chromatograph and Mass Spectrometer Through a Jet Separator," Analytical Chemistry, vol. 50, No. 4, Apr. 1978, pp. 659-660.
Hayes, "Moving Belt Interface with Spray Deposition for Liquid Chromatography/Mass Spectrometry," Anal. Chem. 1983, 55, pp. 1745-1752.

Primary Examiner—Ernest G. Therkorn
Attorney, Agent, or Firm—Shyamala T. Rajender

[57] ABSTRACT

A chromatography column/moving belt interface for directing the output of the column to a point of use, detection and/or identification, such as a mass spectrometer is disclosed. The chromatography column/moving belt interface of this invention thus provides for substantially simultaneous analysis of materials separated in the column. The chromatography column utilizes horizontal flow through the separating medium with the output therefrom being at or near atmospheric pressure. The moving belt interface includes means for directing the output of the column onto a moving belt at variable angles, means for vaporizing output which is deposited on the belt and means for providing a vacuum lock arrangement such that the belt moves from and through a near atmospheric pressure of the column output to a near vacuum condition of the mass spectrometer. The chromatography column may be of a type which has a quickly disposable or replaceable receptacle for the separating medium, such as a thin film member or wafer, or the medium itself or even the entire column may be constructed to be totally disposable or replaceable.

20 Claims, 2 Drawing Sheets

CHROMATOGRAPHY COLUMN/MOVING BELT INTERFACE

BACKGROUND OF THE INVENTION

The present invention is directed to a system separating sample fluid in a chromatography column and directing the effluent of the chromatography column to a point of use, or detection and analysis, particularly to a combination of a chromatography column and an interface for directing the effluent of the chromatography column into a mass spectrometer, and more specifically to a combination of a horizontal flow chromatography column and a moving belt interface therefor.

In a liquid chromatography system, a sample fluid is first injected into a separation column and is followed by flowing an elution fluid therethrough. The separation column contains or is packed with a separation matrix or medium, as is well known in the art, which interacts with the various components of the sample fluid to be separated, and are differentially eluted therefrom using different eluting fluids. The separation columns generally known in the art are of a cylindrical construction and the fluid flows axially through a separating medium bed retained in the column. As the sample and elution fluids pass through the separating medium bed, the constituents of the sample fluid travel through the separation medium at different rates due to their interaction with the separation medium. As a result, these constituents or components emerge separated (i.e., have different elution rates and times) in the effluent or outlet stream of the column. For high performance separations, the use of small particle size packings in long narrow columns has resulted in very high operating pressures.

More recently, this problem of high operating pressures was resolved by employing liquid chromatography columns which utilize a horizontal or radial flow of the fluids through the separation medium in the column, which results in an increased output and in a shorter time, using the same separation medium. Thus, higher flow rates at lower pressures can be achieved using this horizontal flow technique. The horizontal or radial flow liquid chromatography columns are described and claimed in U.S. patent applications Ser. No. 794,727 filed Nov. 4, 1985, now U.S. Pat. No. 4,627,918 and Ser. No. 869,295 filed June 2, 1986, now U.S. Pat. No. 4,676,898, each in the name of Vinit Saxena.

In many applications, it is desirable to analyze and identify the chemical composition of one or more of the components of the sample fluid separated in a liquid chromatographic column, either immediately or shortly thereafter, and more preferably at the same location. Such an analysis and identification may be carried out, for example, in a mass spectrometer. Mass spectrometers are well known for their capability for their sensitivity and accuracy in analyzing various chemicals, but they also have a requirement for a high vacuum environment, such as for example, $10^{-5}$ Torr. The separated fluids discharged from the liquid chromatography columns are, typically, at atmospheric or higher pressures. Various methods and means have been proposed for transporting the column effluent or discharge into the ion source of a mass spectrometer. One such prior known device is the moving belt interface. The fluid discharged from the liquid chromatography column, in addition to being transported to the ion source of the mass spectrometer, must be vaporized for effective ionization thereof and analysis in the ionization chamber of the mass spectrometer.

Various types of moving belt interfaces have been developed, each involving heating of the discharge fluid to vaporize and remove the solvent in the sample as the fluid discharge moves along a moving belt into the ion source of the mass spectrometer, and each providing vacuum locks to maintain the vacuum integrity of the mass spectrometer. While these prior moving belt interface approaches have been successful for certain types of chemicals, they have not been satisfactory in the analyses of certain other types of chemicals including polar, some biological compounds and complex mixtures of certain materials.

Recently, an improved moving belt interface has been developed which provides the capabilities of controlling the speed of the moving belt, controlling the angle at which the material from a source, such as a liquid chromatography column, is directed onto the belt, providing for heating of the material, most intensely only at the tip or end of the belt located within the ion source or any other suitable part of the mass spectrometer, and providing a multiple stage vacuum pumping system which produces the required drop in pressure from near atmospheric to a high vacuum, thereby maintaining the vacuum integrity of the mass spectrometer. This improved moving belt interface is described and claimed in copending U.S. patent application Ser. No. 904,953, , filed Sept. 8, 1986 in the name of Brian D. Andresen.

As greater efforts are now being directed to the field of biotechnology, particularly to more sophisticated methods of biological biomedical analyses, greater needs have arisen for faster, more accurate methods for separating the components of complex mixtures of chemical and biological compounds and for quickly analyzing and identifying such components, while also minimizing the costs of such analyses.

Therefore, it is an object of this invention to provide a means for economically separating the components in a sample fluid and rapidly transporting the same to a point of use or detection, analysis and identification in a mass spectrometer.

A further object of this invention is to provide a combined liquid chromatography column with a moving belt interface for transporting and preparing fluids separated in the column for substantially simultaneous analysis thereof in a mass spectrometer.

Another object of this invention is to provide a method and means for combining a chromatography column, using readily replaceable and/or disposable separation media, with a moving belt interface.

Another object of the invention is to provide a combined horizontal flow chromatographic column and a moving belt interface having the capability of controlling the deposition of materials eluted from the column onto a moving belt.

Another object of the invention is to provide a combined horizontal flow chromatographic column and a moving belt interface with a very short transfer line between the column and the moving belt.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and advantages and in accordance with the purpose of the present invention as embodied and broadly described herein, the instant invention is directed to providing a combined liquid chromatography column and a moving belt interface, wherein the column is of the horizontal or radial flow type having a readily replaceable or disposable separation medium. The combination includes a coupling or attachment mechanism whereby material eluted and discharged from the column is directly deposited on a moving belt at an angle which enables not only the uniform distribution and deposition of the material on the moving belt but also facilitates the instantaneous vaporization or removal of the solvent therefrom as the belt traverses along its path. The column, preferably, is of the type with a thin layer of a separation matrix or in the form of a thin wafer or layer of separation material supported on a solid plate, paper or some other suitable receptacle, or of the type provided with a pair of spaced porous members or frits between which a separation material is retained. The moving belt interface, in addition to including an angle control mechanism for the incoming material from the column, also preferably includes a heated tip or point of return (turnaround point) of the moving belt for vaporizing and/or ionizing the material deposited on the belt at the point of use or detection and identification in the ion source of a mass spectrometer (for example), and means for maintaining the vacuum integrity of an associated mass spectrometer. Thus, the invention provides for substantially simultaneous analysis in a mass spectrometer, of the fluid components separated in a liquid chromatography column. The invention also provides for a vacuum tight connection between the chromatographic column and the mass spectrometer. In addition, the instant invention provides a compact, portable, integral unit, combining a liquid chromatographic column and a moving belt interface for a mass spectrometer, where the transfer line for the sample from the chromatographic column to the moving belt is very short.

DETAILED DESCRIPTION OF THE INVENTION

The present invention involves a combination of a horizontal flow liquid chromatography column and a moving belt interface for directing material separated in the column to a point of use or detection and identification, such as a mass spectrometer. This invention enables substantially simultaneous analysis in a mass spectrometer of material separated in a chromatographic column, the interface providing transport of the separated material while preparing and conditioning it for ionization in the mass spectrometer. The liquid chromatographic column is preferably of a horizontal or radial flow type using easily replaceable or disposable receptacles retaining the separation medium thereon, and which discharges the effluent therefrom directly onto a belt of the moving belt interface. The interface include means for controlling the deposition of the separated material onto the moving belt, vaporizing off the material as it enters the ion source of a mass spectrometer. The interface is also constructed so as to maintain the vacuum integrity of the associated mass spectrometer. The invention provides a means by which a rapid analysis of various separated compounds or components, including polar compounds, biological materials and the like, may be carried out substantially simultaneously with the separation process. The invention provides means by which the chromatographic column and/or the separation medium retained in the column may be easily replaced and/or disposed of, by virtue of the construction of the column and/or the separation medium contained or retained therein.

Figure 1:
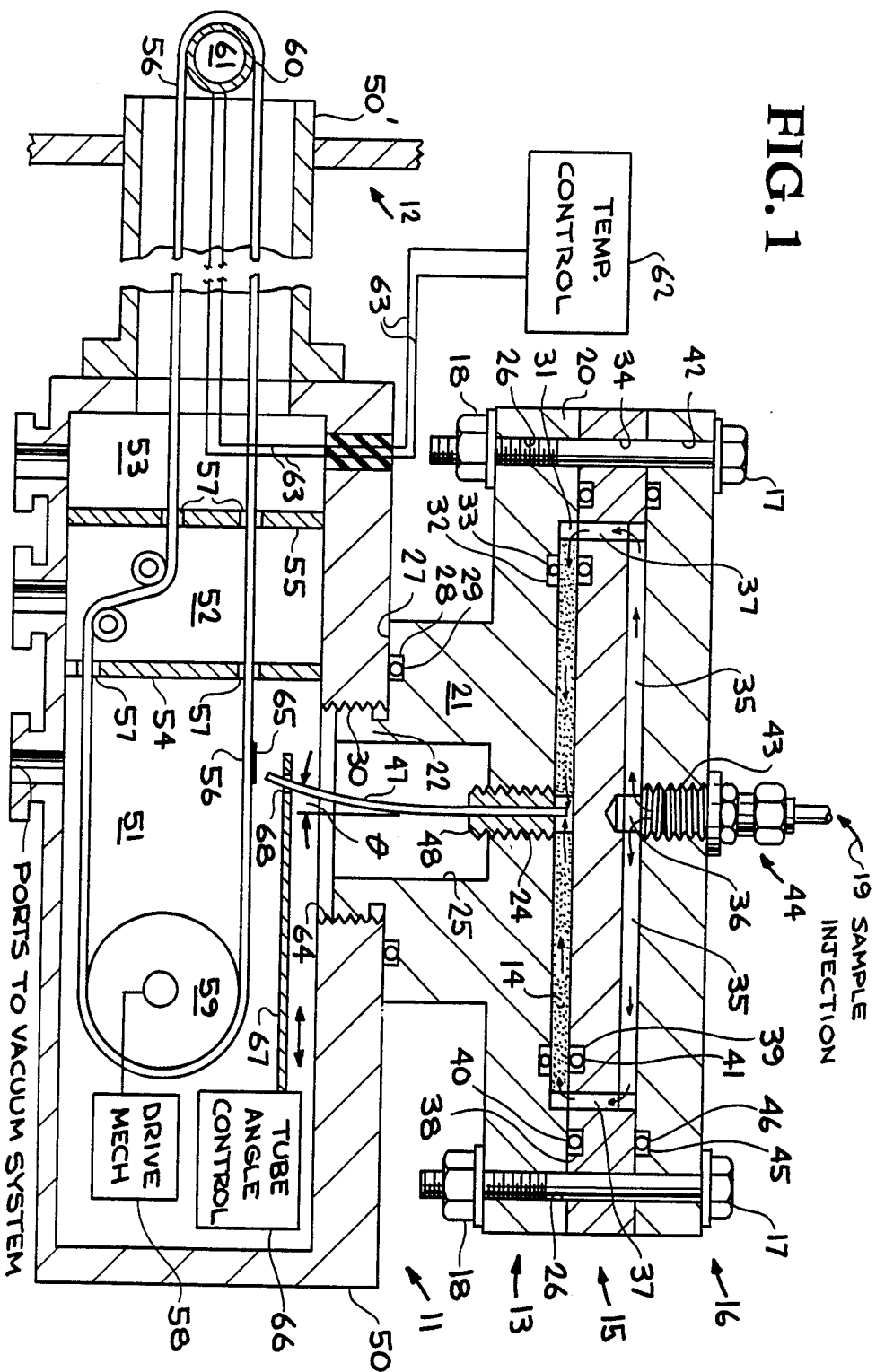
FIG. 1 illustrates an embodiment of the combination of this invention wherein the radial or horizontal flow chromatography column utilizes a disposable or replaceable thin wafer of separation material.

Referring now to FIG. 1, this embodiment illustrates the invention in which a horizontal or radial flow liquid chromatographic column, generally indicated at 10, is directly connected to a moving belt interface, generally indicated at 11, which transports and conditions or prepares the material separated in column 10 to a point of use or detection and identification, such as a mass spectrometer, generally indicated at 12.

The embodiment of the chromatography column illustrated in FIG. 1 basically comprises a lower plate or support member 13, a wafer or thin matrix 14 of separation medium (carried on a thin glass or ceramic plate or a thin piece of filter paper, for example), a distributor plate or member 15, an upper plate or member 16 secured through distributor plate 15 to lower plate 13 by bolts 17 and nuts 18. A sample injection system indicated at 19 is connected to upper plate 16.

The lower plate or support member 13 comprises a body section 20 and two protruding sections 21 and 22 of different diameters, and having an opening extending through all three sections 20, 21 and 22, and having sections 24 and 25 with different diameters, with opening section 24 being threaded. Body section 20 is provided with a plurality of apertures 26 (only two shown) located in spaced relation around the periphery thereof through which bolts 17 extend. Protruding diameter section 21 of plate 13 is provided on an outer edge 27 with a groove 28 in which is located a seal 29, such as an O-ring. Protruding diameter section 22 is provided with threads 30 on the outer surface thereof. Body section 20 of plate 13 is also provided with a countersink 31 in which wafer 14 is positioned, and a groove 32 adjacent countersink 31 in which a seal 33, such as an O-ring made of an inert material, is positioned.

Distributor plate 15 may, for example, be constructed in a manner similar to the sample distribution systems in the earlier referenced applications Ser. Nos. 794,727 and 869,295, which include a plurality of radially extending channels or fluid passageways. Distributor plate 15 in this embodiment is provided around the periphery with a plurality of apertures 34 which align with apertures 26 in lower plate 13 through which bolts 17 extend and a plurality of spaced, radially extending grooves 35 (only two shown), which extend outwardly from a central point 36 and form fluid distribution channels, six channels 35 being utilized in this embodiment. Distribution plate 15 is also provided with a plurality of passages 37 which extend through plate 15 and provide fluid communication between distribution channels or grooves 35 and the periphery of countersink 31 in lower plate 13. Distributor plate 15 is additionally provided with a pair of grooves 38 and 39 located on opposite sides of and spaced from the passages 37 in which are located seals 40 and 41, respectively, such as O-rings.

Upper plate 16 is provided with a plurality of apertures 42 positioned around the periphery so as to align with the apertures in distributor plate 15 and lower plate 13, through which bolts 17 extend. A threaded opening 43 is located in the center of plate 16 and is in alignment with central point 36 of distributor plate 15. A fitting or coupling indicated at 44 is secured in opening 43 and connected to the sample injection system 19. A groove 45 is formed on a lower surface of upper plate 16 in alignment with groove 38 of distributor plate 15, and in which is located a seal 46, such as an O-ring.

A flexible fluid sample component discharge tube 47 is secured at one end by a threaded member 48 secured in threaded opening 24 of lower or support plate 13 and extends outwardly through opening section 25 of plate 13, and is positioned so as to deposit separated fluid components discharged from column 10 onto a belt of moving belt interface 11, as described hereinafter. The various components are combined in a manner so as to render the unit vacuum tight.

With the components of chromatographic column 10 positioned as shown in FIG. 1, sample and elution fluids are injected or fed into column 10 from system 19 via opening 43 in upper plate 16 and travel outwardly through distribution channels or grooves 35, through passages 37 into the periphery of countersink 31 in lower plate 13, whereafter, the sample and elution fluid pass horizontally or radially inward through the separation material wafer or matrix 14, wherein the sample is separated into various constituents or components which then pass into a central opening or collection channel 49 and discharged through tube 47, as indicated by the flow arrows. The constituents or components of the sample fluid so separated within the wafer or matrix 14 emerge at different times into collection channel 49 because of different elution times and rates, as well known in the art of column chromatography. For a further description of the operation of a horizontal or radial flow chromatographic column, if such is desired, reference is made to the copending patent applications Ser. Nos. 794,727 and 869,295 referred to herein earlier.

The wafer or matrix 14 of separation medium may, for example, have a diameter of from about 1½ inches to about 6 inches, preferably about 1½ to about 3 inches, a thickness of about 2 mils to about 50 mils and composed of a thin glass plate, filter paper, ceramic plate and the like on which is coated or deposited a thin, uniform layer of the separation material such as ion exchange resins, reverse phase materials or agarose, sepharose and other cellulosic materials or other separation materials known in the art of chromatography. Precoated or pre-prepared thin layer chromatographic plates of suitable dimensions and with suitable coatings thereon may also be employed. For example, the wafer or matrix 14 may also be made of other polymeric materials such as agarose, sepharose, polyacrylamide, polymethacrylate and the like, or silica gel powder, silver metal powder and/or polyethylene powder or any type of support material and separation medium, the selection of such support material and/or separation medium being dependent on the sample material or fluid to be resolved in column 10.

As can be seen, the column 10 can be readily disassembled to interchange or replace the receptacle containing the separation medium 14 or the medium itself, or the entire column 10 can be quickly disengaged from the moving belt interface 11 and replaced by another column, as desired.

The moving belt interface 11 as illustrated in FIG. 1, includes a housing 50 having therein three chambers 51, 52 and 53 formed by partitions or baffle plates 54 and 55. The chambers 51, 52 and 53 are connected as indicated by legend to a multiple stage vacuum pump, not shown, so constructed as to maintain differential pressures in each of the three chambers, which typically, varies from near atmospheric pressure in chamber 51 to about $10^{-5}$ Torr, for example, in chamber 53.

Housing 50 contains a continuous moving belt 56 which passes through openings or slits 57 in baffle plates 54 and 55, and is driven by a drive mechanism 58 via a wheel, gear or pulley 59 located in housing chamber 51, and rotates around a driven member or roller assembly 60 rotatably mounted by means, not shown, in an outer end of a housing 50' secured to housing 50 around an opening through which belt 56 passes. The end section of housing 50' is located within and secured in a vacuum tight relation to mass spectrometer 12. Drive mechanism 58 may, for example, be of a magnetically coupled type, as described in the copending application Ser. No. 904,953, filed in the name of B. D. Andresen. The moving belt 56 may be constructed of a thin ribbon of mylar, plastic or stainless steel or other material that is compatible with the temperature conditions prevailing and that would be nonreactive with the chemicals and the solvents passing through the interface 11.

The driven member or roller assembly 60 is heated by a heater unit or assembly 61 located within roller assembly 60 and controlled by a temperature controller 62 via an electrical interconnection indicated at 63. The heater assembly heats the roller assembly 60 to a temperature high enough to sublime off the sample components deposited on the belt for ionization and analysis in the mass spectrometer. By way of example, the heater roller 60, heater assembly 61, temperature controller 62 and electrical interconnetion may be of the type described and illustrated in the above-referenced copending application Ser. No. 904,953 filed by Andresen.

Housing 50 is provided with a threaded opening 64 in chamber 51 into which column 10 is mounted via threads 30 of lower plate section 22. Seal 29 is located between lower plate section 21 and an outer surface of housing 50 to provide an air tight and liquid seal therebetween. with column 10 secured to housing 50, as shown, flexible fluid sample component discharge tube 47 of column 10 extends into chamber 51 of housing 50 and terminates adjacent moving belt 56. It has been determined that for the best deposition of the fluid sample components indicated at 65 onto moving belt 56, the discharge tube 47 must be at an angle $\theta$ from the perpendicular with respect to the surface of moving belt 56. Angle $\theta$ will vary with the composition and type of the fluid components 65, the speed at which the belt moves across the end or nozzle of tube 47 and other experimental conditions, but is usually between 20°–30°. To provide control to vary the angle $\theta$ for discharge tube 47, a tube angle control mechanism, generally indicated at 66, is connected to tube 47 via a control rod or member 67 having an opening 68 therein through which the end or nozzle of tube 47 extends. Movement of the control rod 67 in either direction by mechanism 66, as indicated by the double arrow will either increase or decrease the angle $\theta$ as the case may be. The tube angle control mechanism 66, for example, may be of a magnetically coupled type, as described and illustrated in the copending application Ser. No. 904,953 filed by Andresen. The angle $\theta$ may vary from 20° to 30°.

With the column 10 mounted on interface 11 which has a tip or terminal end positioned within the ion source of a mass spectrometer 12, it being understood that interface 11 is secured to mass spectrometer 12 by a vacuum tight coupling mechanism, not shown, fluid components separated in column 10 are be transported, conditioned and prepared by moving belt 11 such that sample 65, for example, is vaporized at the tip of interface 11 by heated roller or mechanism 60 whereby the sample material is vaporized or caused to be sublimed off belt 56. If desired, the sample material 65 may also be ionized by using a fast atom or electron bombardment gun, not shown, by means of which an electron or fast atom beam is made to impinge on the material 65 as the belt 56 passes over roller 60, whereafter the ions so generated are fed or guided into the ion source of the mass spectrometer 12, where they are analyzed and identified. Thus, fluid components separated in column 10 may be directly and substantially simultaneously analyzed by mass spectrometer 12, as a result of the combination of a moving belt interface and a liquid chromatographic column by the interconnection provided by this invention.

Figure 2:
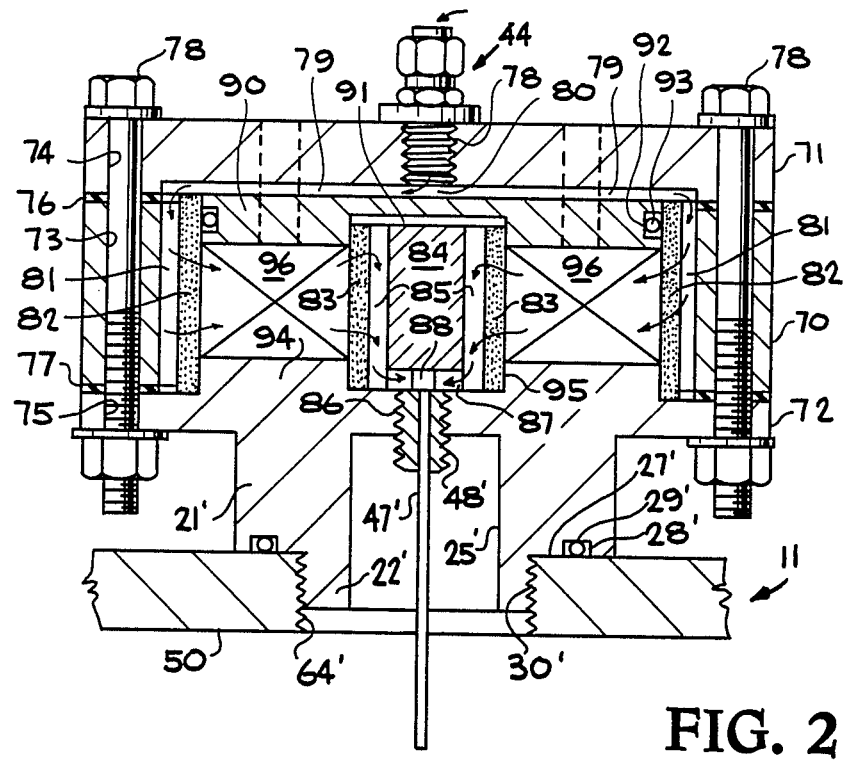
FIGS. 2 and 3 illustrate other embodiment of the horizontal or radial flow chromatographic columns of the combination which utilize a disposable or replaceable receptacles or supports carrying the separation medium retained between the porous frits.

Referring now to FIG. 2 which illustrates another embodiment of a replaceable, horizontal or radial flow chromatographic column, and/or replaceable or disposable receptacles for the separation medium or replaceable or disposable separation medium itself, in said column mounted to the moving belt of the interface 11 of FIG. 1. This column differs from the column of FIG. 1 primarily in the construction of the receptacle for the separation material. In the embodiment of FIG. 2, the separation material is retained between two spaced porous frits rather than being in the form of a wafer or matrix construction. (Like components of FIG. 1 are be given the same corresponding reference numerals in FIG. 2.) The column is composed of a cylindrical body section 70, an upper end cap, plate or section 71 and a lower end cap, plate or section 72. Body section 70 is provided with a plurality of spaced openings or apertures 73 (only two shown), while end caps 71 and 72 are provided with a plurality of openings or apertures 74 and 75, respectively, which correspond to and align with openings 73. A pair of annular seal or gaskets 76 and 77 having openings which align with openings 73 are positioned between body section 70 and end caps 71 and 72. Bolts 78 (only two shown), extend through openings 73, 74 and 75 and gaskets 76 and 77 for securing housing components 70, 71 and 72 together.

As in the embodiment of FIG. 1, upper end cap or plate section 71 is provided with a threaded fluid inlet passage or opening 78 which directs fluid from a source via a coupling 44 to a plurality of distributor grooves or channels 79 (only two shown) via central point 80, grooves or channels 79 terminating adjacent to and providing fluid communication with an annular, longitudinally extending channel 81 formed between an outer porous frit 82 and body section 70. An inner porous frit 83 is snugly positioned around a solid core or member 84 having longitudinally extending grooves or channels 85 (only two shown). The grooves 85 of core 84 are connected to a threaded outlet or collection passage 86 in lower end cap or plate 72 via a plurality of radially extending passages 87 and a central passage 88 in the lower end of core 84. The solid core or member 84 may be constructed, for example, as illustrated in detail in FIG. 4 of the earlier referenced copending application Ser. No. 869,295.

A support plate or member 90 having a central counter-sunk portion 91 and an annular groove 92 for retaining a seal or O-ring 93, is positioned to cooperate with outer frit 82, with inner frit 83, and with solid core 84. Support plate 90 is retained, as shown in FIG. 2, by upper end cap 71.

Lower end cap or plate section 72 is provided with an inwardly protruding section 94 which includes a counter-sunk portion 95 into which, ends of frit 83 and solid core 84 are positioned, with outer frit 82 extending around protruding section 94. A bed 96 of a selected separation medium is located between porous frits 82 and 83, with outer frit 82 being retained between end caps 71 and 72, while inner frit 83 is retained between support plate 90 and lower end cap 72.

In operation of the column of FIG. 2, a sample fluid from a sample injection system, followed by the elution fluid enter inlet passage 78 and flow outwardly through channel 79 to various points around channel 81, whereafter the fluids pass radially or horizontally inward through outer porous frit 82 and through separation medium bed 96 where the sample fluid is separated into its various components by virtue of the different travel and elution times of the various components through the bed 96, and the fluid components pass through passages 87 and 88 into outlet or collection passage 86 into one end of a flexible tube 47' retained in collection passage 86 by a threaded coupling 48', similar to that shown in the embodiment of FIG. 1.

To provide for attachment of the chromatographic column of FIG. 2 onto the housing of a moving belt interface 11, lower end cap or plate section 72 includes an outwardly protruding portion having two different diameter sections 21' and 22', as in the embodiment of FIG. 1, having an opening or aperture 25' through which flexible tube 47' extends. Protruding section 21' is provided on an outer edge 27', with a groove 28' in which is retained a seal or O-ring 29'. Protruding section 22' is provided with threads 30' on the outer surface and is threaded into an opening 64' in housing 50 of moving belt interface 11.

Thus, it is seen that the column of the type illustrated in FIG. 2 has been designed for ready replacement or disposal and is readily attached and disengaged from the moving belt interface 11. The separation medium bed 96 of the column of FIG. 2 can be easily replaced by removal of the retaining bolts 78, upper end cap 71 and support plate 90, whereby the bed 96 and, if desired, the porous frits 82 and 83 can be easily removed and/or replaced. The bed and frits may also be pre-packed and made as a disposable unit.

If desired, the outer porous frit 82 may be provided with a plurality of spaced longitudinally extending grooves on the outer surface thereof, such that the fluid distribution channels or grooves 79 are in fluid communication therewith. The upper and lower end caps or plate sections 71 and 72 may also be secured to column body section 70 via short screws instead of bolts 78, such that either of the end caps 71 or 72 can be removed while leaving the other end cap secured to body section 70. Furthermore, if the head bolts 78 and their nuts or their substitute screws were to be counter-sunk into end caps 71 and 72, the surface would look smooth, without any bumps from the bolts, nuts or screws, and thus facilitate easy stacking of the columns, when and if it is desirable to connect a plurality of columns in series or parallel, for better resolution or higher throughput respectively. For a series connection, the collection output of one column is connected to the material entrance passage of the next column. Thus, with such a stacked system in a series mode, the separation material of each subsequent column may be the same or different and may be selected to separate and resolve only a certain or specific components from the original sample fluid, each desired component being collected and/or siphoned off as the fluid passes through each of the sequence of columns.

Figure 3:
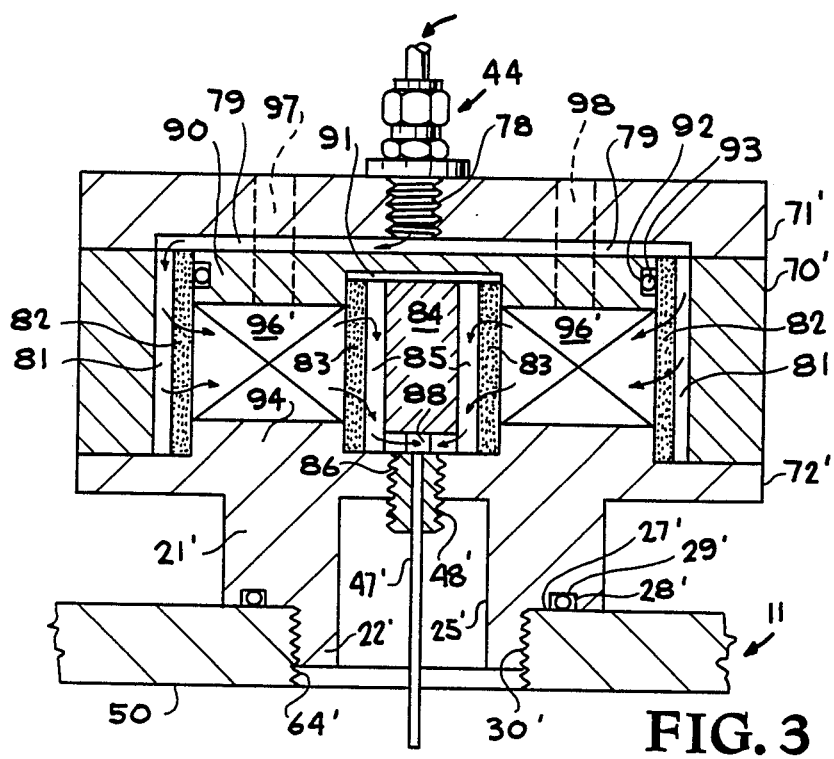

FIG. 3 illustrates an embodiment which is generally similar to that of FIG. 2, with the principal difference being in the manner of construction of the column and in securing together the housing components of the column to make the entire column and the pre-packed separation material therein disposable. In the embodiment of FIG. 3, the housing components, porous frits, and separation medium are made of selected materials and are fabricated to be integral or sealed (glued, bonded or molded as one integral unit) together, whereby the entire column is intended to be disposable.

In FIG. 3, like components or components similar to those of the embodiment of FIG. 2 are given corresponding reference numerals. In FIG. 3, the housing is composed of a cylindrical body section 70', an upper end cap or section 71' and a lower end cap or section 72'. The end caps 71' and 72' are constructed so as to be in abutting relation with body section 70' and are secured together such as by welding, bonding, gluing, molding and the like, thereby eliminating the gaskets 76, 77 and bolts 78 of the embodiment of FIG. 2. This construction also eliminates a great deal of machining requirements, thereby reducing the cost of fabrication considerably. The remainder of the column of FIG. 3 is the same as that of FIG. 2 except that the upper end cap 71' and plate member 90 are provided with a pair of spaced and aligned apertures or ports 97 and 98 which allow for insertion of the separation medium to form a bed within the housing and for the removal of any air trapped within the housing or in the packing material.

The operation of the column of FIG. 3 is substantially the same as for the embodiment of FIG. 2, the difference being in that the entire column of FIG. 3 is disposable after use. The column housing of the embodiment of FIG. 3 is constructed of inexpensive materials, and the components 70' and 71' or 72' may also be integrally molded with the other end cap (71' and 72') being bonded or glued together. Thereafter, the porous frits and core member are positioned within the housing, the separation bed material between the frits being injected through one of the openings, apertures or ports 97 and 98, with air being removed through the other openings 97 and 98. The openings 97 and 98 are then sealed (as by gluing, bonding etc) for the operation of the column.

The materials utilized in the illustrated embodiments of the chromatographic columns discussed herein may be the same as those described in the copending application Ser. No. 794,727, referenced earlier. For example, the column housing and other nonfiltering components may be constructed of material capable of withstanding extreme solvent and temperature conditions, such materials including but not limited to stainless steel, aluminum, titanium, glass, ceramics, teflon, polycarbonate, polysulfone, polypropylene, acrylic and the like. Similarly, the porous frits may be made of polyvinylidene fluoride (PVDF), polypropylene, teflon, stainless steel, polyacetate, polyester, polycarbonate, ceramics, and other porous materials. The separation bed material or medium may be composed of any suitable material that is known and/or employed in the art of chromatographic separations.

It has thus been shown that the present invention enables substantially simultaneous analysis in a mass spectrometer of fluid components separated in a liquid chromatographic column. The combination of a readily removable and/or disposable column and a moving belt interface provided by this invention greatly advances the art in the area of rapid analysis of various types of separated fluid components. The invention provides a compact, portable, integral unit, combining a liquid chromatography column and a moving belt interface for a mass spectrometer, where the transfer line from the column to the moving belt is very short, of the order of 1 to 2", and where the unit is vacuum tight for ready insertion into the ion source of a mass spectrometer. Furthermore, the moving belt interface prepares or conditions the sample material for analysis while transporting it from the column without adversely affecting the composition of the sample material by providing for intense heating of the material only in the area of the ionization thereof. Thus, this invention enables the separation, transport and conditioning or preparing of polar compounds and/or complex mixtures of chemical and/or biological compounds for analysis and identification.

The foregoing description of the embodiments of the invention have been presented for purposes of illustration and description and for a better understanding of the invention. It is not intended to be exhaustive or to limit the invention to the precise form disclosed; and obviously many modifications and variations are possible in light of the above teaching. The particular embodiments were chosen and described in some detail to best explain the principles of the invention and its practical applications to thereby enable others skilled in the relevant art to best utilize the invention in various embodiments and with various modifications as are suited to the particular use contemplated. It is intended that the invention be defined by the claims appended hereto.

What is claimed is:

1. An apparatus for providing direct analysis of a fluid material separated into components, comprising the combination of:

a horizontal flow liquid chromatography column, and a moving belt interface, said chromatography column being removably mounted on said moving belt interface such associated fluid material components separated in said column being deposited directly onto a moving belt located within said interface, said column including disposable separation material, and including a distribution and collection system in which associated fluid material to be separated is adapted to be directed around at least a portion of a periphery of the separation material and pass radially through the separation material with separated fluid components being collected at an opposite periphery of the separation material for discharge onto said belt of said interface, said moving belt interface including means for directing associated fluid components on said belt at an angle $\theta$ from the perpendicular with respect to said belt through a short, flexible tube connected to said column, and including means for heating fluid components on said moving belt only at a point of return of said moving belt and adjacent a point of detection and identification of such fluid components.

2. The apparatus of claim 1, wherein said point of return of said moving belt is located within an ion source of a mass spectrometer, such that said heating means of said moving belt interface causes heating and subliming off the associated fluid components on said moving belt for ionization and analysis in said mass spectrometer.

3. The apparatus of claim 1, wherein the receptacle for said separation material is in the form of a wafer.

4. The apparatus of claim 1, wherein said separation material is positioned intermediate a pair of spaced porous frits.

5. The apparatus of claim 1, wherein said chromatography column includes a lower support member having a protruding section having an opening therein and constructed to be mounted on and secured to a housing of said moving belt interface, said housing having an opening through which extends a flexible tube connected to said collection system of said column for depositing associated separated fluid components on said moving belt, said flexible tube also extending through said opening in said protruding section of said lower support member, said means for directing associated fluid components on said belt including a control mechanism operationally connected to said flexible tube for changing said angle $\theta$.

6. The apparatus of claim 5, wherein said opening in said housing of said moving belt interface is threaded, wherein said protruding section of said lower support member of said column includes an externally threaded portion removably secured in said threaded opening in said housing, and seal means positioned intermediate said protruding section of said lower support member and said housing.

7. The apparatus of claim 6, wherein said protruding section of said lower support member includes a plurality of portions each of said portions having a different cross-section, said externally threaded portion being located on a smaller of said different cross-section portions, said seal means being located intermediate an outer surface of a larger of said different cross-section portions, and said housing.

8. The apparatus of claim 7, wherein said seal means consists of an O-ring located in a groove formed in said outer surface of said larger of said different cross-sections portions of said protruding section of said lower support member.

9. The apparatus of claim 5, wherein said control mechanism for changing said angle $\theta$ includes a movable member operationally connected at one end to an outer end of said flexible tube, and means for moving said movable member in different directions for increasing or decreasing said angle $\theta$.

10. The apparatus of claim 9, wherein said means for heating fluid components on said moving belt includes:

a roller assembly around which said moving belt passes, heating means located in said roller assembly, and control means operationally connected to said heating means, whereby said heating means causes heating of said roller assembly which causes heating and subliming off fluid components on said moving belt as said moving belt passes over said roller assembly.

11. The apparatus of claim 10, wherein at least said roller assembly and said heating means are positioned within a mass spectrometer secured to said moving belt interface.

12. The apparatus of claim 10, wherein said housing of said moving belt interface is provided with a plurality of chambers therein, each of said chambers being connected to a multiple-stage pump system for controlling pressure within each of said chambers, said flexible tube extending into one of said plurality of chambers, said means for heating fluid components on said moving belt being located in another of said plurality of chambers.

13. The apparatus of claim 12, wherein said housing includes a portion having a smaller cross-section, said means for heating fluid components on said moving belt being located in said smaller cross-section portion of said housing.

14. The apparatus of claim 13, wherein said roller assembly is located in an outer end of said smaller cross-section housing portion.

15. The apparatus of claim 14, wherein said plurality of chambers in said housing are formed by a pair of spaced members located within said housing and secured thereto so as to maintain vacuum integrity between said chambers, said spaced members being provided with means through which said moving belt passes.

16. The apparatus of claim 12, additionally including a drive mechanism for said moving belt, said drive mechanism including means located in said one of said plurality of chambers around which said moving belt passes.

17. The apparatus of claim 1, wherein said liquid chromatography column is of a disposable type.

18. In a system consisting of a liquid chromatography column, a moving belt interface, and a mass spectrometer, the improvement comprising:

means for removably mounting directly on a housing of said moving belt interface, at least one chromatography column, which utilizes horizontal flow of liquid through the separation medium contained therein, means for controlling an angle $\theta$ between a short, flexible discharge tube connected to said column and a moving belt located in said interface, and means for heating said moving belt only at an end thereof which is located within said mass spectrometer, whereby fluid components separated in said column are directed through said flexible tube and a selected angle $\theta$ onto said moving belt, and heated only at said end of said moving belt located within said mass spectrometer causing subliming off for ionization, detection and analysis thereof in said mass spectrometer.

19. The improvement of claim 18, wherein said chromatography column is constructed so as to be readily disassembled and contains a disposable separation medium.

20. The improvement of claim 18, wherein said chromatography column is of a disposable type.

* * * * *